(12) United States Patent
Chaplin (10) Patent No.: US 11,466,278 B2
(45) Date of Patent: Oct. 11, 2022

(54) TEMPERATURE BASED PLASMID REGULATION SYSTEM

(71) Applicant: Novo Nordisk A/S, Bagsvaerd (DK)

(72) Inventor: Jay Chaplin, Mountlake Terrace, WA (US)

(73) Assignee: Novo Nordisk A/S, Bagsvaerd (DK)

( * ) Notice: Subject to any disclaimer, the term of this patent is extended or adjusted under 35 U.S.C. 154(b) by 225 days.

(21) Appl. No.: 16/341,940

(22) PCT Filed: Nov. 1, 2017

(86) PCT No.: PCT/EP2017/077959
§ 371 (c)(1),
(2) Date: Apr. 15, 2019

(87) PCT Pub. No.: WO2018/083116
PCT Pub. Date: May 11, 2018

(65) Prior Publication Data
US 2019/0241898 A1    Aug. 8, 2019

Related U.S. Application Data

(60) Provisional application No. 62/415,717, filed on Nov. 1, 2016.

(30) Foreign Application Priority Data

Jan. 2, 2017   (EP) .................................. 17150037
May 2, 2017   (EP) .................................. 17169019
Jun. 22, 2017  (EP) .................................. 17177289
Oct. 24, 2017  (EP) .................................. 17198041

(51) Int. Cl.
*C12N 15/70*   (2006.01)
*C12N 15/65*   (2006.01)
*C12N 15/64*   (2006.01)

(52) U.S. Cl.
CPC ............. *C12N 15/70* (2013.01); *C12N 15/64* (2013.01); *C12N 15/65* (2013.01)

(58) Field of Classification Search
CPC ........ C12N 15/70; C12N 15/65; C12N 15/64; C12N 2800/10
See application file for complete search history.

(56) References Cited

U.S. PATENT DOCUMENTS

| | | | |
|---|---|---|---|
| 6,083,919 A | 7/2000 | Johnson et al. | |
| D459,798 S | 7/2002 | Desesquelle et al. | |
| 7,544,669 B2 | 6/2009 | Fontoura et al. | |
| 9,339,500 B2 | 5/2016 | Wennogle | |
| 9,550,998 B2 | 1/2017 | Williams | |
| D835,258 S | 12/2018 | Parikh et al. | |
| 10,487,334 B2 | 11/2019 | Audonnet et al. | |
| 11,279,745 B2 | 3/2022 | Chaplin et al. | |
| 2002/0107210 A1 | 8/2002 | Herrath | |
| 2002/0193330 A1 | 12/2002 | Hone et al. | |
| 2003/0148983 A1 | 8/2003 | Fontoura et al. | |
| 2004/0110295 A1 | 6/2004 | Punnonen et al. | |
| 2004/0234984 A1 | 11/2004 | Isaksson et al. | |
| 2005/0026189 A1 | 2/2005 | Wang et al. | |
| 2005/0147621 A1 | 7/2005 | Higgins et al. | |
| 2005/0261215 A1 | 11/2005 | Garren et al. | |
| 2006/0234964 A1 | 10/2006 | Strober et al. | |
| 2009/0016968 A1 | 1/2009 | Wang et al. | |
| 2009/0042301 A1 | 2/2009 | Owttrim et al. | |
| 2010/0160415 A1 | 6/2010 | Solvason et al. | |
| 2011/0034543 A1 | 2/2011 | Steinman et al. | |
| 2014/0234423 A1 | 8/2014 | Sands et al. | |
| 2018/0117133 A1 | 5/2018 | Chaplin et al. | |
| 2020/0339650 A1 | 10/2020 | Chaplin et al. | |

FOREIGN PATENT DOCUMENTS

| | | |
|---|---|---|
| JP | 2012527249 A | 11/2012 |
| JP | 2014526472 A | 10/2014 |
| RU | 2228198 | 5/2004 |
| WO | 9824469 A1 | 6/1998 |
| WO | 2005089101 A2 | 9/2005 |
| WO | 2007016764 A1 | 2/2007 |
| WO | 07147011 A2 | 12/2007 |
| WO | 11091138 A1 | 7/2011 |
| WO | 12041867 A2 | 4/2012 |
| WO | 2012062697 A1 | 5/2012 |
| WO | 2013036914 | 3/2013 |
| WO | 2014144965 | 9/2014 |
| WO | 2016057986 | 4/2016 |
| WO | 2016162385 A1 | 10/2016 |
| WO | 2017097383 A1 | 6/2017 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Chinnasamy et al . . . "Multicistronic lentiviral vectors containing the FMDV 2A cleavage factor demonstrate robust expression of encoded genes at limiting MOI." Virology Journal, Mar. 2006, vol. 3, No. 1, pp. 1-14.
Bot et al., Plasmid Vaccination with Insulin B Chain Prevents; Autoimmune Diabetes in Nonobese Diabetic Mice, The Journal of Immunology, 2001, vol. 167, pp. 2950-2955.
Harrison C et al., Vaccination against self to prevent autoimmune; disease: the type 1 diabetes model, Immunology and Cell Biology, 2008, vol. 86, pp. 139-145.
Johnson C. et al., Genetic vaccination for re-establishing T-cell tolerance; in type 1 diabetes, Human Vaccines, 2011, vol. 7, No. 1, pp. 27-36.
Prud'Homme et al., DNA vaccines that induce regulatory T cells and protect against autoimmune diabetes, Gene Ther Mol Biol, 2005, vol. 9, pp. 183-192.
Prud'Homme et al., Plasmid-based gene therapy of diabetes mellitus, Gene Therapy, 2007, vol. 14, pp. 553-564.

(Continued)

*Primary Examiner* — Iqbal H Chowdhury
(74) *Attorney, Agent, or Firm* — Jianjie Hu (57) ABSTRACT

The present invention relates to a recombinant *E. coli* cell harbouring a recombinant plasmid wherein said *E. coli* cell has a thermo sensitive regulation of an essential *E. coli* gene.

18 Claims, 5 Drawing Sheets

(56) References Cited

OTHER PUBLICATIONS

Roep et al., Plasmid-Encoded Proinsulin Preserves C-Peptide WhileSpecifically Reducing Proinsulin-Specific CD8+ T Cells in Type 1 Diabetes, www.ScienceTranslationalMedicine.org, 2013, vol. 5, No. 191, pp. 191ra82.

Sarikonda et al., "Transient B-Cell Depletion with Anti-CD20 in Combination with Proinsulin DNA Vaccine or Oral Insulin: Immunologic Effects and Efficacy in NOD Mice," PLoS One, 2013, vol. 8, No. 2, p. e54712.

Solvason et al., Improved Efficacy of a Tolerizing DNA Vaccine for Reversal; of Hyperglycemia through Enhancement of Gene Expression; and Localization to Intracellular Sites, The Journal of Immunology, 2008, vol. 181, pp. 8298-8307.

Coppieters et al., "Trials in Type 1 Diabetes: Antigen-Specific Therapies," Clinical Immunology, 2013, vol. 149, No. 3, pp. 345-355.

Gottlieb et al., "Clinical Optimization of Antigen Specific Modulation of Type 1 Diabetes with the Plasmid DNA Platform," Clinical Immunology, 2013, vol. 149, No. 3, pp. 297-306.

Torres-Aguilar et al., "IL-10/TGF-I-Treated Dendritic Cells Pulsed with Insulin, Specifically Reduce the Response to Insulin of CD4+ Effector/Memory T Cells from Type 1 Diabetic Individuals," Journal of Clinical Immunology, 2010, vol. 30, No. 5, pp. 659-668.

Yu et al., Identification of Candidate Tolerogenic CD8 + T Cell Epitopes for Therapy of Type 1 Diabetes in the NOD Mouse Model, Journal of Diabetes Research, 2016, vol. 2016, pp. 1-12.

Muller S. et al., "Spliceosomal peptide P140 for immunotherapy of systemic lupus erythematosus: results of an early phase II clinical trial," Arthritis & Rheumatism: Official Journal of the American College of Rheumatology, Dec. 2008, vol. 58, No. 12, pp. 3873-3883.

Croitoru et al., "Generation and characterization of functional mutants in the translation initiation factor IF1 of *Escherichia coli*," Eur J Biochem., 2004, vol. 271, No. 3, pp. 534-544.

Goransson et al., "Regulatory genes in the thermoregulation Of *Escherichia coli* pili gene transcription," Genes & Development, 1989, vol. 3, pp. 123-130.

Goransson et al., "Transcriptional silencing and thermoregulation of gene expression in *Escherichia coli*," Nature, 1990, vol. 34, p. 682-685.

Hägg et al., "A host/plasmid system that is not dependent on antibiotics and antibiotic resistance genes for stable plasmid maintenance in *Escherichia coli*," J Biotechnol., 2004, vol. 111, No. 1, pp. 17-30.

Johansson et al., "An RNA thermosensor controls expression of virulence genes in *Listeria monocytogenes*," Cell, 2002, vol. 110, No. 5, pp. 551-561.

Matsunaga et al., "Role for cis-Acting RNA Sequences in the Temperature-Dependent Expression of the Multiadhesive Lig Proteins in Leptospira Interrogans," Journal of Bacteriology, 2013, vol. 195, No. 22, pp. 5092-5101.

Sodoyer et al., "Antibiotic-Free Selection for Bio-Production: Moving Towards a New "Gold Standard,"" Apr. 4, 2012, pp. 531-538.

Waldminghaus et al., "Generation of Synthetic RNA-based Thermosensors," Biological Chemistry, 2008, vol. 389, No. 10, abstract.

Loh et al., "An unstructured 5'-coding region of the prfA mRNA is required for efficient translation", Nucleic Acids Research, Nov. 3, 2011, vol. 40, No. 4, pp. 1818-1827.

Kitani et al., "Transforming Growth Factor (TGF)-ß1-producing Regulatory T Cells Induce Smad-mediated Interleukin 10 Secretion That Facilitates Coordinated Immunoregulatory Activity and Amelioration of TGF-ß1-mediated Fibrosis", The Journal of Experimental Medicine, Oct. 13, 2003, vol. 198, No. 8, pp. 1179-1188.

\* cited by examiner

Passages 1-50.

Passages 51-100.

TEMPERATURE BASED PLASMID REGULATION SYSTEM

CROSS-REFERENCE TO RELATED APPLICATIONS

This application is a 35 U.S.C. § 371 National Stage application of International Application PCT/EP2017/077959 (WO 2018/083116), filed Nov. 1, 2017, which claims priority to European Patent Applications 17150037.4, filed Jan. 2, 2017, 17169019.1, filed May 2, 2017, 17177289.0, filed Jun. 22, 2017, 17198041.0, filed Oct. 24, 2017, and claims further priority to U.S. Patent Application 62/415,717, filed Nov. 1, 2016; the contents of which are incorporated herein by reference.

TECHNICAL FIELD

The present invention relates to recombinant E. coli cells having a temperature based plasmid selection system.

BACKGROUND

A key pressure in biopharmaceutical manufacture is the regulatory drive to move away from any use of antibiotics for selection or maintenance of transfected cells. Beyond introducing significant materials costs and process impurities, antibiotic resistance genes incorporated into plasmids result in significant regulatory hurdles for nucleic acid based therapies due to potential transfer to patients or the environment.

Compensation systems, where necessary genes are deleted from the host cell genome and supplied in trans by the plasmid, are a common compromise and replacement for antibiotic resistance systems. In order to produce vector-free host cells, most compensation systems rely on knockouts of metabolic genes (such as dapD or pyrF) and corresponding introduction of the required metabolic intermediates for growth (auxotrophy using lysine amino acid or uracil nucleoside base, respectively) until plasmids containing the compensating gene are introduced. Once the gene has been compensated by the plasmid, growth in minimal media will occur for plasmid-containing cells only and exert a selective pressure for the plasmid's retention. Unfortunately, while such selection is robust at low cell densities, plasmid containing hosts produce and secrete an overabundance of the required metabolic intermediate and allow for cross-feeding at high cell densities. In cross feeding, plasmid containing cells support the growth of plasmid deficient cells and reduce the overall efficiency of the selection system during industrial processes.

In contrast, selection of essential non-metabolic target genes for complementation results in both stable and stringent maintenance of plasmids but results in a "locked" phenotype—such as with infA/IF-1 complementation (Hägg et al. J Biotechnol. 2004; 111(1):17-30). In this case the genomically deleted protein (IF-1) is required for protein production by stabilizing the first step of translation—deletion of the infA gene (and consequently, the IF-1 protein) is therefore obligately lethal to the bacterium and occurs even if IF-1 is supplied in the media, as there is no uptake pathway for rescue of infA deficient cells, thus preventing cross-feeding. Any engineered host cell which even transiently loses its compensating plasmid dies rapidly. While this maintains stringent selection, it also means that there is no possibility of propagating plasmid-free host cells, and therefore no way to introduce new plasmids or further modify the system—therefore the phenotype is "locked" and useless for downstream modification or production purposes.

Croitoru et al. Eur J Biochem 271 (2004) 534-544, discloses a range of functional mutants of translational initiation factor IF1 of Escherichia coli. Replacement of the genomic infA gene with these slow growth mutants of infA would result in a growth advantage for plasmid complemented cells but lacks stringent selection that would eliminate plasmid deficient cells. As such, a system with these characteristics would always contain a significant proportion of plasmid-free biomass and result in lowered industrial yields of plasmid than current antibiotic-based selection systems.

Metabolic (auxotrophic) complementation is well known but results in relaxed stringency during high density industrial culture environments. Other complementation strategies work well for plasmid maintenance but are inflexible "single-use" systems. Hence, there is a need for complementation systems which are suitable for industrial use and which are flexible systems allowing repetitive rounds of modifications to optimize the system.

SUMMARY

In a first aspect the present invention provides a recombinant E. coli cell comprising a genomically encoded essential E. coli gene where expression is regulated by an upstream leader sequence not natively associated with said essential E. coli gene, where said upstream leader sequence has the function of being a thermoswitch substantially not allowing growth at a first temperature but allowing growth at a second temperature.

In a second aspect the present invention provides a
  method for maintaining a plasmid in a recombinant E. coli comprising the insertion of a recombinant plasmid into a recombinant E. coli cell wherein
    said recombinant E. coli cell comprises a genomically encoded essential E. coli gene which expression is regulated by an upstream leader sequence not natively associated with said essential E. coli gene, where said upstream leader sequence has the function of being a thermoswitch substantially not allowing growth at a first temperature but allowing growth at a second temperature, and
    said recombinant plasmid comprises an essential E. coli gene encoding a protein having the same or substantially the same function as said essential E. coli gene genomically encoded by said E. coli cell, thus allowing growth at both temperatures.

In one embodiment the recombinant E. coli cell according to the invention comprises a plasmid encoding an essential E. coli gene encoding a protein having the same or substantially the same function as said essential E. coli gene genomically encoded by said recombinant E. coli cell.

In one embodiment said genomically encoded essential E. coli gene is infA or a functional equivalent thereof.

In one embodiment said upstream leader sequence comprises the mRNA leader sequence from L. monocytogenes prfA or a functional equivalent thereof.

By placing the genomic copy of an essential gene under environmental (temperature) control we provide a system where stringent selection and maintenance can be achieved through culture at a selective temperature and where empty (plasmid free) host cells can be propagated and expanded for future use at a permissive temperature. This allows for downstream flexibility (ability to use the same host strain for

DESCRIPTION

The present invention provides a modified cell line which is capable of replication under permissive temperatures, while also being inviable at non-permissive temperatures unless complemented with a compensatory plasmid. Such cell line/plasmid systems provide ease of downstream use with stringent industrial selection.

In a first aspect the present invention provides a recombinant E. coli cell comprising a genomically encoded essential E. coli gene where expression is regulated by an upstream leader sequence not natively associated with said essential E. coli gene, where said upstream leader sequence has the function of being a thermoswitch substantially not allowing growth at a first temperature but allowing growth at a second temperature.

The term "substantially not allowing growth at a first temperature" as used herein is intended to mean not allowing growth at any significant rate as compared to normal growth at said first temperature, i.e. at a growth rate less than 30% of the normal growth rate, at less than 10% of normal growth rate or less than 1% of normal growth rate. Conversely, the term "allowing growth at a second temperature" as used herein is intended to mean allowing growth at a rate which is substantially the same as the normal growth rate at said second temperature In a second aspect the present invention provides a method for maintaining a plasmid in a recombinant E. coli comprising the insertion of a recombinant plasmid into a recombinant E. coli cell wherein said recombinant E. coli cell comprises a genomically encoded essential E. coli gene which expression is regulated by an upstream leader sequence not natively associated with said essential E. coli gene, where said upstream leader sequence has the function of being a thermoswitch substantially not allowing growth at a first temperature but allowing growth at a second temperature, and said recombinant plasmid comprises an essential E. coli gene encoding a protein having the same or substantially the same function as said essential E. coli gene genomically encoded by said E. coli cell, thus allowing growth at both temperatures.

In one embodiment the recombinant E. coli cell according to the invention comprises a plasmid encoding an essential E. coli gene encoding a protein having the same or substantially the same function as said essential E. coli gene genomically encoded by said recombinant E. coli cell.

In one embodiment said genomically encoded essential E. coli gene is infA or a functional equivalent thereof.

In one embodiment said upstream leader sequence comprises the mRNA leader sequence from L. monocytogenes prfA or a functional equivalent thereof.

The term "functional equivalent thereof" as used herein is intended to mean an alternative which exhibits substantially the same main function.

To correct for the unmodifiable phenotype of the infA/IF-1 complementation system of Hägg et al., we utilized the L. monocytogenes prfA mRNA leader. In L. monocytogenes the prfA leader segment functions as a thermosensor to control translation of a key invasion protein—prohibiting translation at environmental temperatures under 30° C. (on surfaces, in foodstuffs, etc.) but allowing translation of the mRNA at temperatures of 37° C. (once consumed by a suitable host). The mRNA leader accomplishes this by folding over upon itself and forming a stable hairpin at 30° C. which occludes the ribosomal binding site and AUG initiation codon. This structure melts and unfolds at temperatures above 37° C. (physiologic temperatures for potential hosts), thus allowing ribosomal binding and translation (Johansson et al. Cell. 2002 (110) 551-61). While thermosensor RNA leader segments of pathogenic bacteria are evolutionarily tuned to temperature transitions which are industrially useful (30° C. to 37° C., L. monocytogenes prfA and Y. pestis lcrF) there are many other potential options available for such constructs. For example, ROSE (Repressor Of heat-Shock gene Expression) elements, FourU element of S. enterica, rpoH of E. coli, hsp17 of the cyanobacterial Synechocystis, hsp90 of D. melanogaster, and the cIII of bacteriophage lambda ($\lambda$) all contain similar RNA-thermosensor motifs. While these elements inhibit translation below permissive temperatures they are used to prevent translation of heat shock proteins at normal temperatures and the permissive temperatures for these systems are not useful for bacterial fermentation (commonly in excess of 42° C.). Conversely, cold shock RNA-thermosensors exist where mRNA stability is adversely impacted by partial folding and nuclease sensitivity under normal physiological conditions but is stabilized and allows mRNA accumulation and translation following more extensive and compact folding below 25° C. While these systems are not directly useful, it is anticipated that modifying these elements, or designing fully synthetic elements based on their principles (Waldminghaus, et. al. Biol Chem. 2008 389:1319-26), can provide alternative thermosensors with desired properties.

Temperature-based control of the essential infA host gene is thus achieved by replacing the upstream genomic sequence in the E. coli cell line with the mRNA leader sequence from L. monocytogenes prfA or an equivalent translational control mechanism. As these regions functionally block translation of the fused IF-1/infA gene product at temperatures of 30° C. or below, it rapidly induces death of the engineered host unless the gene is complemented in trans from a plasmid which may also contain a production gene-of-interest. Any approach to integrate a thermosensor equivalent to the L. monocytogenes prfA upstream of a small, essential gene of E. coli could be expected to have the same performance. While many genes are considered "essential" for E. coli, most are condition specific and lose their requirement under many rich media, slow growth, or alternate metabolic systems—only a small fraction are truly essential and result in complete cellular elimination upon removal. A variety of truly essential non-metabolic E. coli genes other than infA may be selected for complementation systems, such as infC/IF-3, dnaJ, dnaK, era, frr, ftsL, ftsN, ftsZ, grpE, mopA, mopB, msbA, nusG, parC, rpsB, or trmA may be used as alternatives. Of these alternatives small genes are preferable due to restrictions on size of the complementing plasmids, leading to a ranked preference of infA, mopB, ftsL, infC, nusG, frr, and grpE based on gene length as the other candidate genes are, on average, over three times the length and complexity.

In this arrangement (prfA leader segment fused 5' to the genomic infA copy), four amino acids are added to the N-terminus of IF-1 and the translation of the fusion is regulated by the temperature of the fermentation environment. At permissive temperatures (37° C. and above) plasmid-free host cells can grow due to unfolding of the prfA leader and translation of the infA gene to IF-1, allowing for further protein synthesis and cellular survival. At stringent selection temperatures (25° C. to 30° C.) the prfA leader remains folded, thus preventing further protein synthesis and rapidly leading to the death of plasmid-free host cells.

As a further, and surprising, benefit the four amino acids added to the fusion due to the prfA leader (MNAQ) reduce efficiency of the fusion IF-1 product without fully compromising its activity—as a result while plasmid-free host cells may be propagated at permissive temperatures (37° C. and above), they do so with a roughly two to four-fold increase in doubling time. This results in an additional and unexpected "soft-selection" wherein plasmids containing the native infA confer a substantial growth advantage to the engineered host cells even under the most permissive culture conditions. It is anticipated that other small modifications of essential genes, such as the infA mutants disclosed in Croitoru, et. al. Eur J Biochem 271 (2004) 534-544, may exist which would also improve the selection efficiency of these systems (decreasing duration of low temperature exposure required for selection, further reducing growth rate at permissive temperatures, etc.). While such modifications alone cannot result in complete deselection of plasmid deficient bacteria, they may be included to optimize selection performance in combination with RNA-based translational controls.

Other desirable features of these essential gene complementation systems include the lack of providing any selective advantage for wild-type bacteria—therefore minimizing the likelihood of environmental persistence following undesirable horizontal gene transfer (HGT, a key regulatory agency concern).

Our reduction to practice was to utilize standard recombination technology to specifically introduce the native *L. monocytogenes* prfA leader sequence (5' end through the first four amino acids of PrfA, 127 bp) in place of the native *E. coli* infA mRNA leader which occurred upstream of the initiating AUG codon—thus creating a temperature controlled hybrid fusion of the essential gene IF-1 (or infA::prfA).

Following this, the host strain can be propagated in an "empty" or receptive state by growth at a permissive temperature of 37° C., though with a four-fold growth rate defect. Once a complementing plasmid containing the gene of interest as well as a native infA ORF is supplied the growth temperature can be dropped to 30° C. and all plasmid-deficient host cells will rapidly die and a strong selective pressure for retention of the plasmid will be enacted. Even when grown at the fully permissive temperature of 37° C. there is a growth advantage for plasmid containing cells as the four amino acid PrfA/IF-1 fusion has inferior activity to the native IF-1 supplied by complementing plasmids.

The following embodiments illustrate the invention and are not to be understood in any limiting way.

1. A recombinant *E. coli* cell comprising a genomically encoded essential *E. coli* gene where expression is regulated by an upstream leader sequence not natively associated with said essential *E. coli* gene, where said upstream leader sequence has the function of being a thermoswitch substantially not allowing growth at a first temperature but allowing growth at a second temperature.
2. A recombinant *E. coli* cell comprising a genomically encoded essential *E. coli* gene where expression is regulated by an upstream leader sequence not natively associated with said essential *E. coli* gene, where said upstream leader sequence has the function of being a thermoswitch substantially not allowing growth at a first temperature but allowing growth at a second temperature without native gene complementation.
3. The recombinant *E. coli* cell according to any of the preceding embodiments wherein said recombinant *E. coli* cell comprises no further genomically encoded versions of said essential *E. coli* gene.
4. The recombinant *E. coli* cell according to any of the preceding embodiments which comprises a plasmid encoding an essential *E. coli* gene encoding a protein having the same or substantially the same function as said essential *E. coli* gene genomically encoded by said *E. coli* cell.
5. The recombinant *E. coli* cell according to embodiment 4 wherein said essential *E. coli* gene encoded by said plasmid encodes a gene product having higher activity in said recombinant *E. coli* cell than said genomically encoded essential *E. coli* gene.
6. The recombinant *E. coli* cell according to any of the preceding embodiments wherein said upstream leader sequence comprises the mRNA leader sequence from *L. monocytogenes* prfA or a functional equivalent thereof.
7. The recombinant *E. coli* cell according to any of the preceding embodiments wherein said essential *E. coli* gene encodes a protein involved in transcription or translation.
8. The recombinant *E. coli* cell according to any of the preceding embodiments wherein said genomically encoded essential *E. coli* gene is infA or a functional equivalent thereof.
9. The recombinant *E. coli* cell according to embodiment 8 wherein the protein expressed from said infA or a functional equivalent thereof has a lower activity than the protein (IF1) encoded by the native *E. coli* infA.
10. The recombinant *E. coli* cell according to any of embodiments 8-9 wherein said infA or a functional equivalent thereof has the peptide MNAQ as its N-terminal sequence.
11. The recombinant *E. coli* cell according to any of embodiments 5-10 wherein said essential *E. coli* gene encoded by said plasmid is native *E. coli* infA.
12. The recombinant *E. coli* cell according to any of embodiments 5-11 wherein the growth rate of said *E. coli* cell at any temperature permitting growth is higher when said essential *E. coli* gene is mainly expressed from the plasmid rather than mainly or solely from said genomically encoded essential *E. coli* gene.
13. The recombinant *E. coli* cell according to any of the preceding embodiments, wherein said first temperature is lower than said second temperature.
14. The recombinant *E. coli* cell according to any of the preceding embodiments, wherein the difference between said first temperature and said second temperature is at least about 1° C., at least about 2° C., at least about 5° C., or at least about 7° C.
15. The recombinant *E. coli* cell according to any of the preceding embodiments, wherein said first temperature is about 30° C. and said second temperature is about 37° C.
16. The recombinant *E. coli* cell according to embodiment 15, wherein said first temperature is in the range from 27° C. to 33° C. and said second temperature is in the range from 34° C. to 40° C.
17. A method for maintaining a plasmid in a recombinant *E. coli* comprising the insertion of a recombinant plasmid into a recombinant *E. coli* cell wherein
said recombinant *E. coli* cell comprises a genomically encoded essential *E. coli* gene which expression is regulated by an upstream leader sequence not natively associated with said essential *E. coli* gene, where said upstream leader sequence has the function of being a thermoswitch substantially not allowing growth at a first temperature but allowing growth at a second temperature, and
said recombinant plasmid comprises an essential *E. coli* gene encoding a protein having the same or substantially the same function as said essential *E. coli* gene genomically encoded by said *E. coli* cell, thus allowing growth at both temperatures.
18. The method according to embodiment 16 wherein said recombinant *E. coli* cell is as defined in any of claims 4-16.

EXAMPLES

Example 1

To preclude contamination with previous plasmid variants utilizing the pVAX1 kanamycin resistance selection marker, one ICC vial was scraped twice and used to separately inoculate kanamycin or naladixic acid containing animal-free LB agar plates. Plates were incubated at 37° C. for 17 hours prior to examination. No growth was observed on the kanamycin plate, indicating no parental pVAX1 vector was present to confound analysis.

Passages 1-100 of the engineered host (infA::prfA) containing an infA complementing plasmid were generated at 11 per week, 2 (12 hour) passages per weekday at 37° C. and one (48 hour) each weekend @ 30° C. As the standard doubling time for *E. coli* in LB media is 20-30 minutes, each weekday passage reflects 24 rounds of cell division. All passages were performed in liquid animal-free LB media supplemented with 15 micrograms/ml naladixic acid (selecting for DH5a base strain, not for plasmid presence). Glycerol stocks were generated from each passage and retained until all 100 passages were obtained for concurrent processing.

Scrapes of the glycerol stocks were used to inoculate 5 ml overnight cultures which were processed via supplier instructions on Qiagen miniprep kits using a vacuum manifold (either 16 or 32 cultures per run, due to gel size constraints). No attempt was made to collect OD600 readings for cell input normalization and all preparations were made based on standard volumes. One microliter of each miniprep was subjected to PstI/XhoI digestion to resolve backbone (approximately 2.4 Kbp) from insert (approximately 4 Kbp), without correction for plasmid concentration resulting from each miniprep. Each gel was run with flanking Tridye 2-Log ladders, a first sample lane of undigested plasmid, and all samples were visualized with SybrSafe dye. Despite lack of control for nucleic acid quantity, all digest lanes show both the presence and expected digestion pattern for plasmid These results demonstrate stable and long-term maintenance of the plasmid though this selection system.

Glycerol stocks for passages 1-100 were also streaked onto 50 sector antibiotic-free and animal-free LB agar plates and incubated overnight at 30° C. No attempt to control for streak inoculum was made. All glycerol stock representative streaks resulted in noticeable growth, and thus plasmid retention. No growth was seen for plates streaked with plasmid-deficient host cells. These results also demonstrate effective maintenance of the plasmid through this selection system and the lack of generation of escape mutants during long-term passaging.

Plasmid drift was determined via full Sanger sequencing of plasmid (6,383 base pairs) isolated from passage 1 and passage 100. Sequencing was performed with double stranded reads at a minimum of 2× depth and re-run if integrity was questionable. No significant drift was detected (<1 ambiguous base call per 1,000 bp; no multi-base changes, inversions, additions, or deletions; within read-error tolerance for the equipment and protocol). These results demonstrate that the selection system does not introduce significant mutational or recombination stress on the plasmid which would be deleterious for industrial plasmid production, the plasmid is sequence stable through over 2,400 rounds of cell division.

Plasmid persistence in engineered (infA::prfA) vs. unmodified host cells was performed without antibiotic selection by triplicate transfection of chemically competent *E. coli* cells with either the previously used infA complementing plasmid or a mock transfection. Cells were seeded into 250 mL shake flasks and cultured for 10 hours before sampling for plasmid DNA yield via Qiagen miniprep. Under these conditions few initial cells are expected to be positive for plasmid and rapid plasmid loss is expected without positive selective pressure—as plasmid maintenance slows growth due to the added metabolic requirements and adds its own negative selective pressure to plasmid containing cells. Mean DNA (plasmid) yields all exhibited std. errors of approximately 0.02 μg. This demonstrates that the infA-complementing plasmid is not persistent in wild type *E. coli* or to be expected if environmentally released.

TABLE 1

| Host cell | DH5α | DH5α | DH5α infA::prfA | DH5α infA::prfA |
|---|---|---|---|---|
| Plasmid type | None/mock | infA-complementing | None/mock | infA-complementing |
| DNA yield | 0.039 μg | 0.057 μg | 0.040 μg | 12.8 μg |

Example 2

Verification of Plasmid Retention with infA Complementation System.

In order to verify that the infA-based plasmid retention selection system functioned as desired, the plasmid transformed bacteria were grown through 100 passages (roughly 36 doublings/generations per passage, for a total of 3,600 generations of potential drift or plasmid loss examined). Passages 1-100 were generated at 11 per week, 2 passages per weekday at 37° C. and one each weekend @ 30° C. All were performed in liquid animal-free LB media (Teknova soy-tone) supplemented with 15 micrograms/ml naladixic acid (selecting for DH5a base strain, not for plasmid presence). Glycerol stocks were generated from each passage and retained until all 100 passages were obtained for concurrent processing. Scrapes of the glycerol stocks were used to inoculate 5 ml overnight cultures which were processed via supplier instructions on Qiagen miniprep kits using a vacuum manifold (either 16 or 32 cultures per run, due to gel size constraints). No attempt was made to collect OD600 readings for cell input normalization and all preps were done based on standard volumes. One microliter of each miniprep was subjected to PstI/XhoI digestion to resolve backbone (approximately 2.4 Kbp) from insert (approximately 4 Kbp), without correction for plasmid concentration resulting from each miniprep. Each gel was run with flanking Tridye 2-Log ladders, a first sample lane of undigested plasmid, and visualized with SybrSafe dye. In FIGS. 1-4, despite lack of control for nucleic acid quantity, all digest lanes show both the presence and expected digestion pattern for plasmid. (See FIGS. 1-4 for passages 1-16, 17-48, 49-80, and 81-100, respectively.)

Figure 1:
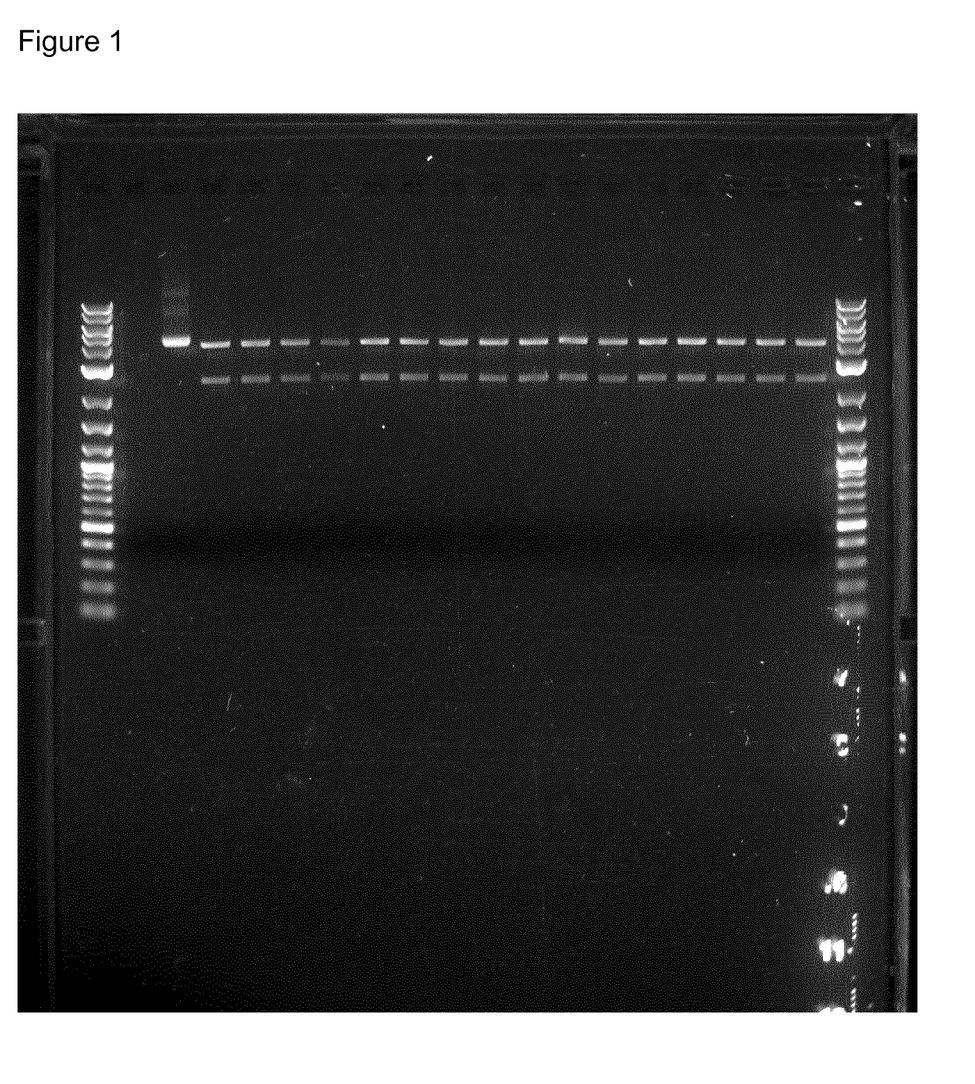
FIG. 1. Restriction digest confirmation of plasmid retention, samples 1-16.
Figure 2:
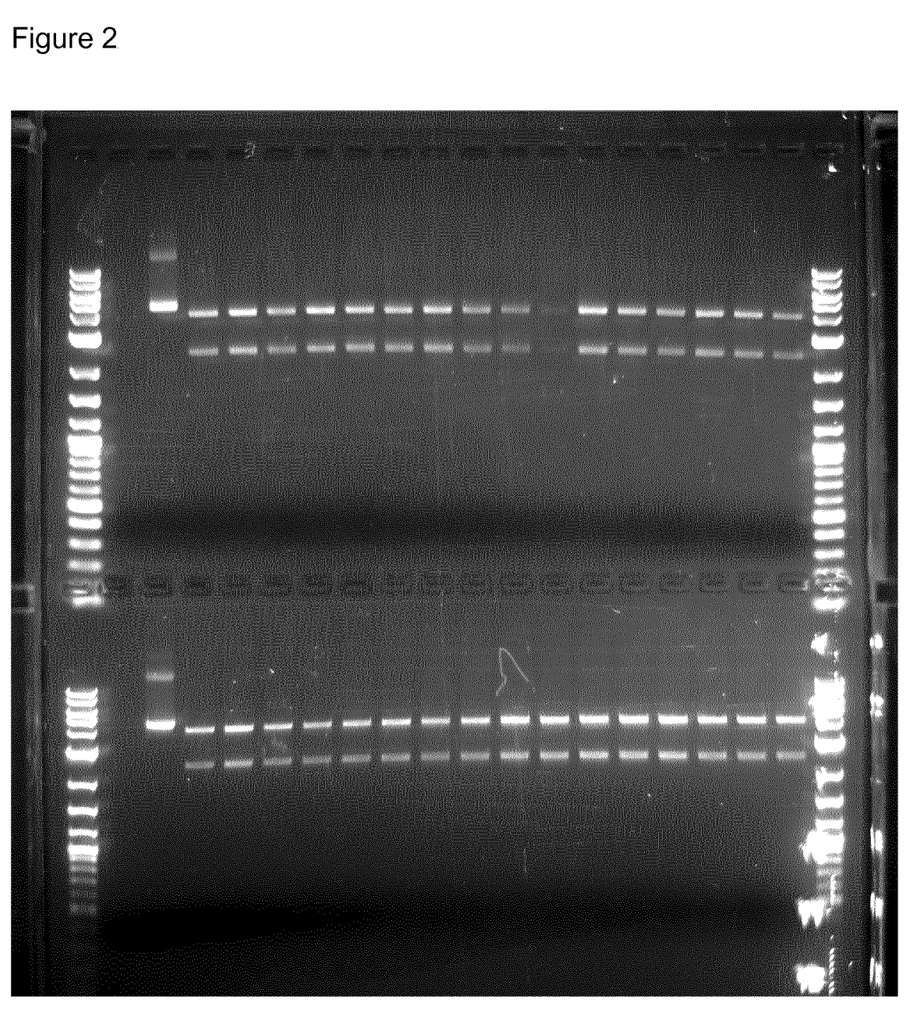
FIG. 2. Restriction digest confirmation of plasmid retention, samples 17-48.
Figure 3:
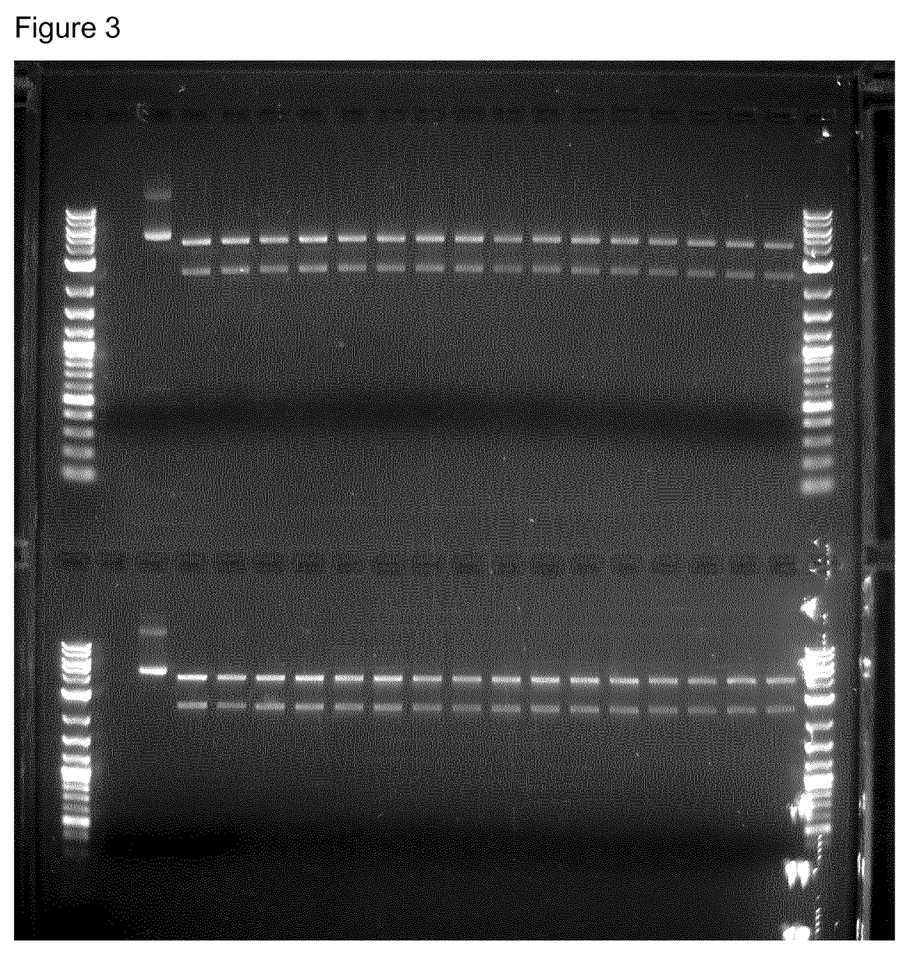
FIG. 3. Restriction digest confirmation of plasmid retention, samples 49-80.
Figure 4:
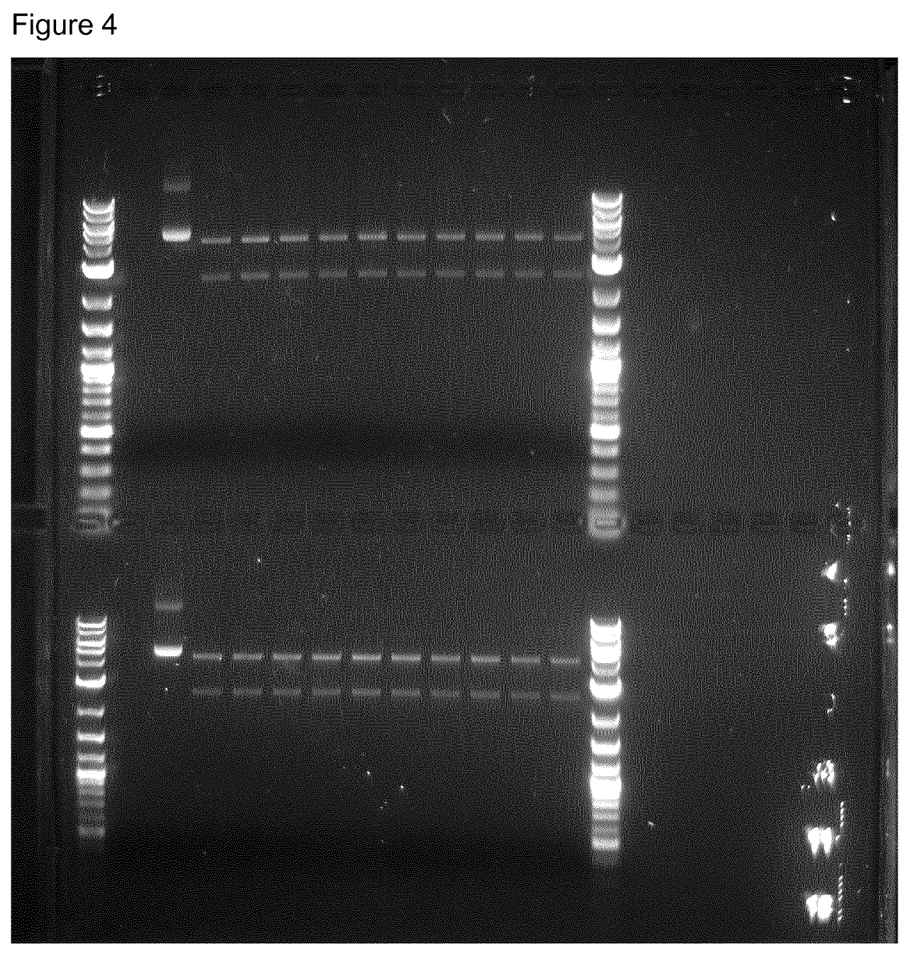
FIG. 4. Restriction digest confirmation of plasmid retention, samples 81-100.
Figure 5:
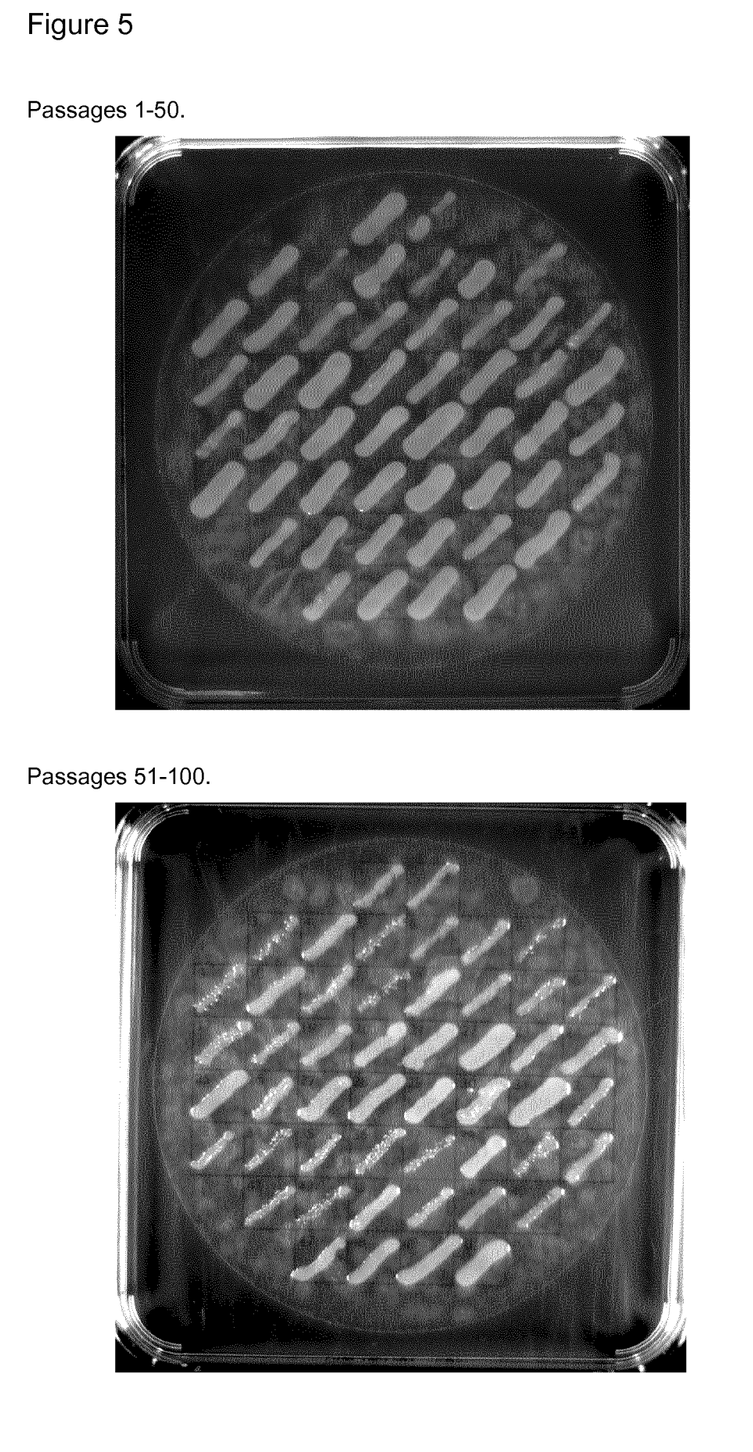
FIG. 5. Confirmation of plasmid retention phenotype by growth at 30° C. (samples 1-50, 17 hours incubation; samples 51-100, 22 hours incubation).

As an additional confirmation, glycerol stocks for passages 1-100 were also streaked onto 50 sector antibiotic-free and animal-free LB agar plates and incubated overnight at 30° C. No attempt to control for streak inoculum was made. As shown in FIG. 5, all glycerol stock representative streaks resulted in noticeable growth and thus plasmid retention.

Example 3

Suitability for Scale Up with infA Complementation System.

In order to verify that the infA-based plasmid retention selection system functioned as desired at production scale, the plasmid transformed bacteria were used in a 50 L pilot fed-batch fermentor run with a specific yield enhancing temperature shift step. Minimal medium with the addition of yeast extract was utilized, reducing the doubling rate to 0.88/hour. The fed-batch was initiated at 17h00 post inoculation and the regulation of dissolved oxygen at 30% was realized by successive increase of the pO2 cascade parameters (stirring at 32h15, pressure at 40h30 then air flow at 45h40). The biomass increase rate lessened immediately following the shift to 42° C., as anticipated. The amount of plasmid DNA produced was estimated at 1.03±0.17 g/L using a small scale plasmid extraction procedure mimicking immediate post-lysis yield.

The invention claimed is:

1. A recombinant *E. coli* cell comprising a genomically encoded essential *E. coli* gene, where expression is regulated by an upstream leader sequence not natively associated with said genomically encoded essential *E. coli* gene, where said upstream leader sequence has the function of being a thermoswitch substantially not allowing growth at a first temperature but allowing growth at a second temperature, wherein said genomically encoded essential *E. coli* gene is infA, mopB, ftsL, infC, nusG, fa, or grpE, and wherein said upstream leader sequence comprises the mRNA leader sequence from *L. monocytogenes* prfA or the mRNA leader sequence from *Y. pestis* lcrF.

2. A recombinant *E. coli* cell comprising a genomically encoded essential *E. coli* gene where expression is regulated by an upstream leader sequence not natively associated with said genomically encoded essential *E. coli* gene, where said upstream leader sequence has the function of being a thermoswitch substantially not allowing growth at a first temperature but allowing growth at a second temperature without native gene complementation, wherein said genomically encoded essential *E. coli* gene is infA, mopB, ftsL, infC, nusG, frr, or grpE, and wherein said upstream leader sequence comprises the mRNA leader sequence from *L. monocytogenes* prfA or the mRNA leader sequence from E *pestis* lcrF.

3. The recombinant *E. coli* cell of claim 1, wherein said recombinant *E. coli* cell comprises no further genomically encoded versions of said essential *E. coli* gene.

4. The recombinant *E. coli* cell of claim 1, which comprises a plasmid comprising an essential *E. coli* gene encoding a protein having the same function as a protein encoded by said genomically encoded essential *E. coli* gene.

5. The recombinant *E. coli* cell of claim 4, wherein said essential *E. coli* gene of said plasmid encodes protein having higher activity in said recombinant *E. coli* cell than said protein of said genomically encoded essential *E. coli* gene.

6. The recombinant *E. coli* cell of claim 1, wherein said upstream leader sequence comprises the mRNA leader sequence from *L. monocytogenes* prfA.

7. The recombinant *E. coli* cell of claim 1, wherein said genomically encoded essential *E. coli* gene encodes a protein involved in transcription or translation.

8. The recombinant *E. coli* cell of claim 1, wherein said genomically encoded essential *E. coli* gene is infA.

9. The recombinant *E. coli* cell of claim 8 wherein the protein expressed from said infA has a lower activity than the protein encoded by the native *E. coli* infA.

10. The recombinant *E. coli* cell of claim 5, wherein said essential *E. coli* gene of said plasmid is native *E. coli* infA.

11. The recombinant *E. coli* cell of claim 5, wherein the growth rate of said *E. coli* cell at any temperature permitting growth is higher when said essential *E. coli* gene is mainly expressed from the plasmid rather than mainly or solely from said genomically encoded essential *E. coli* gene.

12. The recombinant *E. coli* cell of claim 1 wherein said first temperature is lower than said second temperature.

13. The recombinant *E. coli* cell of claim 1, wherein the difference between said first temperature and said second temperature is at least 1° C.

14. The recombinant *E. coli* cell of claim 1, wherein said upstream leader sequence comprises the mRNA leader sequence from *Y. pestis* lcrF.

15. The recombinant *E. coli* cell of claim 1, wherein said genomically encoded essential *E. coli* gene is infA, mopB, ftsL, infC, nusG, frr, or grpE.

16. The recombinant *E. coli* cell of claim 1, wherein said upstream leader sequence further comprises the first four amino acids of *L. monocytogenes* prfA.

17. A method for maintaining a plasmid in a recombinant *E. coli* comprising the insertion of a recombinant plasmid into a recombinant *E. coli* cell wherein
said recombinant *E. coli* cell comprises a genomically encoded essential *E. coli* gene which expression is regulated by an upstream leader sequence not natively associated with said essential *E. coli* gene, where said upstream leader sequence has the function of being a thermoswitch substantially not allowing growth at a first temperature but allowing growth at a second temperature, wherein said genomically encoded essential *E. coli* gene is infA, mopB, ftsL, infC, nusG, frr, or grpE, and
wherein said upstream leader sequence comprises the mRNA leader sequence from *L. monocytogenes* prfA or the mRNA leader sequence from E *pestis* lcrF, and
said recombinant plasmid comprises an essential *E. coli* gene encoding a protein having the same function as said essential *E. coli* gene genomically encoded by said *E. coli* cell, thus allowing growth at both temperatures.

18. A method for maintaining a plasmid in a recombinant *E. coli* comprising the insertion of a recombinant plasmid into a recombinant *E. coli* cell wherein said recombinant *E. coli* cell comprises a genomically encoded essential *E. coli* gene which expression is regulated by an upstream leader sequence not natively associated with said essential *E. coli* gene, where said upstream leader sequence has the function of being a thermoswitch substantially not allowing growth at a first temperature but allowing growth at a second temperature, wherein said upstream leader sequence comprises the mRNA leader sequence from *L. monocytogenes* prfA or the mRNA leader sequence from *Y. pestis* lcrF, and said recombinant plasmid comprises an essential *E. coli* gene encoding a protein having the same function as said essential *E. coli* gene genomically said *E. coli* cell, thus allowing growth at both temperatures, wherein said recombinant *E. coli* cell is as defined in claim 4.

* * * * *

UNITED STATES PATENT AND TRADEMARK OFFICE
CERTIFICATE OF CORRECTION

PATENT NO. : 11,466,278 B2
APPLICATION NO. : 16/341940
DATED : October 11, 2022
INVENTOR(S) : Jay Chaplin It is certified that error appears in the above-identified patent and that said Letters Patent is hereby corrected as shown below:

In the Claims

At Column 10, Claim number 2, Line number 4-5, please replace "from E pestis IcrF" to "from Y. pestis IcrF"

At Column 10, Claim number 17, Line number 65, please replace "from E pestis IcrF" to "from Y. pestis IcrF"

Signed and Sealed this
Second Day of May, 2023

Katherine Kelly Vidal
*Director of the United States Patent and Trademark Office*